US008511301B2

(12) United States Patent
Nobutani et al.

(10) Patent No.: US 8,511,301 B2
(45) Date of Patent: Aug. 20, 2013

(54) LIQUID FORMULATION EJECTION DEVICE

(75) Inventors: Toshiyuki Nobutani, Yokohama (JP); Mitsuru Imai, Chichibu (JP)

(73) Assignee: Canon Kabushiki Kaisha, Tokyo (JP)

( * ) Notice: Subject to any disclaimer, the term of this patent is extended or adjusted under 35 U.S.C. 154(b) by 1134 days.

(21) Appl. No.: 12/063,515

(22) PCT Filed: Sep. 7, 2006

(86) PCT No.: PCT/JP2006/318207
§ 371 (c)(1),
(2), (4) Date: Feb. 11, 2008

(87) PCT Pub. No.: WO2007/032411
PCT Pub. Date: Mar. 22, 2007

(65) Prior Publication Data
US 2009/0145431 A1   Jun. 11, 2009

(30) Foreign Application Priority Data
Sep. 13, 2005   (JP) ................................ 2005-264535

(51) Int. Cl.
*A61M 15/00*   (2006.01)

(52) U.S. Cl.
USPC .................................. 128/203.14; 128/203.12

(58) Field of Classification Search
USPC ............. 128/200.14–200.24, 203.12, 203.25; 239/289, 340, 343
See application file for complete search history.

(56) References Cited

U.S. PATENT DOCUMENTS

| 8,100,123 | B2 * | 1/2012 | Belson | 128/204.15 |
| 2005/0093919 | A1 * | 5/2005 | Takatsuka et al. | 347/30 |
| 2005/0190240 | A1 * | 9/2005 | Takatsuka | 347/68 |
| 2005/0231564 | A1 * | 10/2005 | Nakamura et al. | 347/80 |
| 2005/0275687 | A1 * | 12/2005 | Furuichi et al. | 347/43 |
| 2007/0062520 | A1 | 3/2007 | Nobutani et al. | 128/200.14 |
| 2007/0125370 | A1 * | 6/2007 | Denyer et al. | 128/200.14 |
| 2007/0227534 | A1 | 10/2007 | Nobutani et al. | 128/200.14 |
| 2007/0240706 | A1 | 10/2007 | Kobayashi et al. | 128/200.14 |
| 2008/0011292 | A1 | 1/2008 | Sugita et al. | 128/200.19 |
| 2008/0022998 | A1 | 1/2008 | Hamano et al. | 128/200.14 |

FOREIGN PATENT DOCUMENTS

| JP | 2004-97617 A1 | 4/2004 |
| JP | 2004097617 A * | 4/2004 |
| JP | 2004-283244 A1 | 10/2004 |
| WO | WO 95/01137 A1 | 1/1995 |
| WO | WO 02/04043 A2 | 1/2002 |

OTHER PUBLICATIONS

Int'l Search Report mailed Nov. 7, 2008, for International Application No. PCT/JP2006/318207.

(Continued)

*Primary Examiner* — Justin Yu
*Assistant Examiner* — Rachel Young
(74) *Attorney, Agent, or Firm* — Fitzpatrick, Cella, Harper & Scinto

(57) ABSTRACT

There is provided a liquid formulation ejection device which improves reliability of inhalation even in a case where a preejection is performed and resolves a concern about hygiene. The liquid formulation ejection device (1) ejects a liquid formulation in a form of liquid droplets into an inhalation flow path (20) and allows a user to inhale the formulation. The liquid formulation ejection device (1) includes an ejector (11) for performing normal liquid droplet ejection for inhalation and liquid droplet preejection not for inhalation, and a discharger (13, 14, 28) for removing liquid droplets ejected by the liquid droplet preejection out of an inside of the inhalation flow path (20).

4 Claims, 6 Drawing Sheets

(56) References Cited

OTHER PUBLICATIONS

Written Opinion of the International Searching Authority mailed Nov. 7, 2008, for International Application No. PCT/JP2006/318207.
Int'l Search Report mailed Nov. 7, 2006, for International Application No. PCT/JP2006/318207.
Written Opinion of the International Searching Authority mailed Nov. 7, 2006, for International Application No. PCT/JP2006/318207.
Japanese Office Action dated May 31, 2011, issued in counterpart Japanese Patent Application No. 2005/264535, with translation.
Office Action issued Mar. 2, 2012, in counterpart Canadian Patent Application No. 2,618,829.

* cited by examiner

LIQUID FORMULATION EJECTION DEVICE

This application is a National Stage filing under 35 U.S.C. §371 of International Application No. PCT/JP2006/318207, filed Sep. 7, 2006.

TECHNICAL FIELD

The present invention relates to a liquid formulation ejection device such as a drug ejection device which is so configured as to be portably carried by a user and ejects a drug as fine droplets allowing the user to inhale the drug.

BACKGROUND ART

In recent years, the average life expectancy has been increasing to thereby increase the elderly population because of the advances in medicine and science. However, the change in dietary habits or living environments and the environmental pollution have increased, and new illness and infectious diseases due to viruses or fungi have appeared, so that anxiety to the health of the people has been increasing. Particularly, in the so-called advanced nations, the increase of patients of life-style related diseases such as diabetes mellitus, hypertension or the like has become a problem.

On the other hand, since the number of medical institutions has not so increased as to cope with such increase of patients, and since there are communities where there is no medical institution which patients can attend, there is a concern for how to cope therewith, also from the viewpoint of public policy.

Description will be made below with reference to a specific example. Of the diabetes mellitus patients who are increasing at present, the so-called insulin-dependent type (type I) diabetes mellitus patients have no secretion of insulin from their pancreas and need to be regularly administered with insulin. Because insulin is administered by subcutaneous injection at present, the physical and mental labor of patients is large.

In order to reduce the labor of such users, a pen-shaped injection syringe has been developed which has a thin needle and gives less pain to a patient. However, because most of the I-type diabetes mellitus patients work as with an able-bodied person except for requiring regular administration of insulin. Therefore, they have mental resistance to injection in public even with a pen-shaped injection syringe, so that it is difficult to administer insulin at a proper time. As a result, with such a method, there is a possibility that the users may not be treated appropriately.

On the other hand, a treatment for a user in which a drug ejection device for allowing the user to intake the drug through inhalation is utilized in combination with information database such as electronic medical records is being embodied. Such a drug ejection device also serves as a personal digital assistant that is provided with both a storage means for storing information related to an individual user including information on the medical record and prescription of the user and an inhaler for ejecting the drug in the form of fine liquid droplets to allow the user to inhale the drug. Further, the drug ejection device includes, in order for the user to inhale the drug according to the information of the prescription, an ejection control means for controlling, based on an inhalation profile, the inhaler to eject the drug (refer to International Publication Nos. WO 95/01137 and WO 02/04043).

Such a drug ejection device can accurately manage the dose and frequency of administration of the drug according to the prescription, performs appropriate ejection control in accordance with the inhalation profile of an individual user, and can effectively administer the drug. According to such a drug ejection device, since it is not required to use a conventional medical instrument such as an injection syringe when administering the drug, it is possible not only to easily operate the device without expert knowledge, but also to diminish the pain by a needle of an injection syringe of a user.

Meanwhile, appropriate means for dealing with an operation failure of a drug ejection unit or the like is in demand. For example, in a case where a user has a chronic disease and requires regular administration of a drug, the administration and management of the drug depends on the reliability of the drug ejection device and the appropriate operation by the user. In this case, there is a need for provision of a function of somehow notifying the user of an operational failure of the device including a drug ejection unit, a physical attachment error of a consumable part, or the like.

Further, even in a case where the drug ejection unit in the drug ejection device is attached normally, when it is necessary for the user to bring the drug ejection device with him, there is a possibility of causing ejection failure due to battery exhaustion or the like. Still further, it is known that in order to obtain, through inhalation of liquid droplets of insulin from a drug ejection device, the same effect as that obtained when administering insulin to a human body through injection, ejection of liquid droplets with a particle diameter of about 3 μm is required. Accordingly, the size of an ejection orifice is necessarily reduced, thereby posing a possibility of ejection failure due to clogging of the ejection orifice.

Therefore, there has been proposed, as means for resolving the problem of such ejection failure, a method of performing preejection of liquid droplets before inhalation to improve the ejection reliability (see Japanese Patent Application Laid-Open No. 2004-97617).

However, when performing the preejection before the inhalation, the drug liquid droplets float in an inhalation flow path, so there is a possibility of inhaling the preejected drug and the drug for inhalation together at a time of the inhalation. In some drugs, even a small difference in amount may result in a large difference in the effect thereof, and there are cases where the amount of inhaled drug must be strictly controlled.

Further, since a drug contains much protein, there is a possibility that adherence of protein to an inside wall of an inhalation flow path may result in generation of mold or putrefaction, thereby posing a concern about hygiene. In order to resolve such concern, it is required for users themselves, medical institutions, manufacturers, or the like to perform continuous cleaning, disinfection, or maintenance.

DISCLOSURE OF THE INVENTION

In view of the above-mentioned problems, it is an object of the present invention to provide a liquid formulation ejection device which ensures reliability of inhalation even in a case where a preejection is performed and resolves a concern about hygiene.

The liquid formulation ejection device according to the present invention is for ejecting a liquid formulation in a form of liquid droplets into an inhalation flow path and allowing a user to inhale the drug.

The liquid formulation ejection device comprises an ejector for performing normal liquid droplet ejection for inhalation and liquid droplet preejection not for inhalation, and a discharger for removing liquid droplets ejected by the liquid droplet preejection out of an inside of the inhalation flow path.

With the above-mentioned configuration, by the provision of the discharger, it is possible to remove the liquid droplets ejected by the preejection conducted before the inhalation out of the inside of the inhalation flow path. Further, in a case where the discharger is so configured as to collect the liquid droplets removed from the inside of the inhalation flow path, the liquid droplets ejected by the preejection can be prevented from leaking out of the inhalation flow path and the device. In such configuration, the discharger has, for example, a discharge flow path connected to the inhalation flow path, an exhaust means for guiding the liquid droplets to the discharge flow path (for example, an exhaust fan), a portion provided in the discharge flow path, for collecting the liquid droplets (for example, a liquid-droplet collecting filter).

According to the present invention, by providing the liquid formulation ejection device with the discharger, it is possible to improve the reliability of inhalation even when performing the preejection. Further, the concern about hygiene is resolved.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Preferred embodiments of the present invention will now be described in detail in accordance with the accompanying drawings.

EXAMPLES

Figure 1:
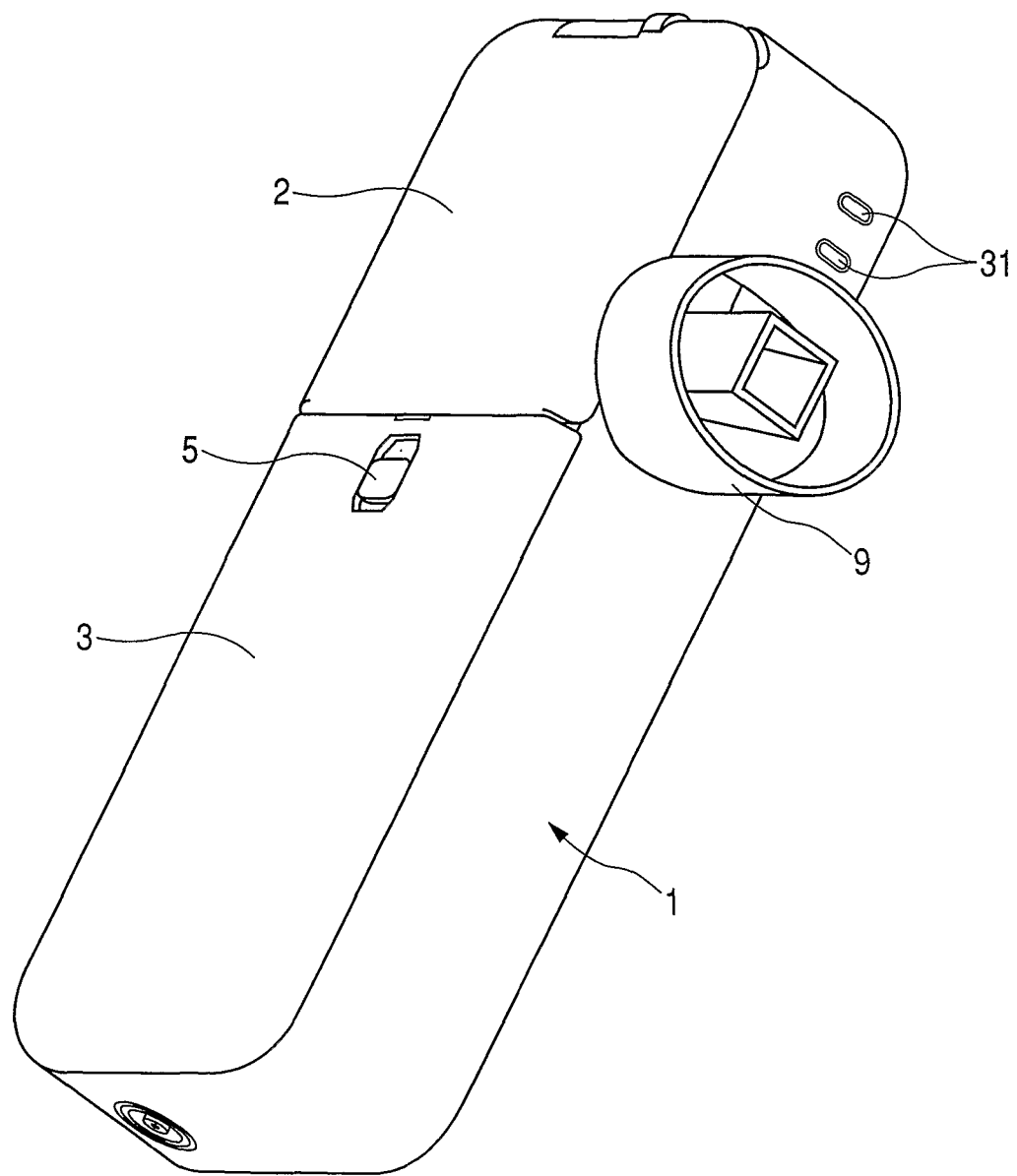
FIG. 1 is a perspective view for illustrating an example of the ejection device according to the present invention.

FIG. 1 is a perspective view showing an external appearance of an example according to the present invention. In the figure, reference numeral 1 denotes a device main body, reference numeral 2 denotes an access cover, reference numeral 3 denotes a front cover, and a housing is composed of these components. Reference numeral 5 denotes a lock lever which engages with a protrusion provided on an end of the access cover 2 such that the access cover 2 does not open in use. In order to achieve the locking, the lock lever 5 is formed such that a claw-shaped portion provided at the front edge of the lock lever 5 urged by a spring engages with the protrusion of the access cover 2. When sliding the lock lever 5 downwardly, the access cover 2 opens with a hinge axis 7 (shown in FIG. 2) being used as a rotation center by the force of an access-cover-returning spring 6 urging the access cover 2. Moreover, reference numeral 31 denotes a display LED which displays that an ejection unit or mouthpiece described later is not mounted or that no liquid formulation remains in a tank of the ejection unit.

Figure 2:
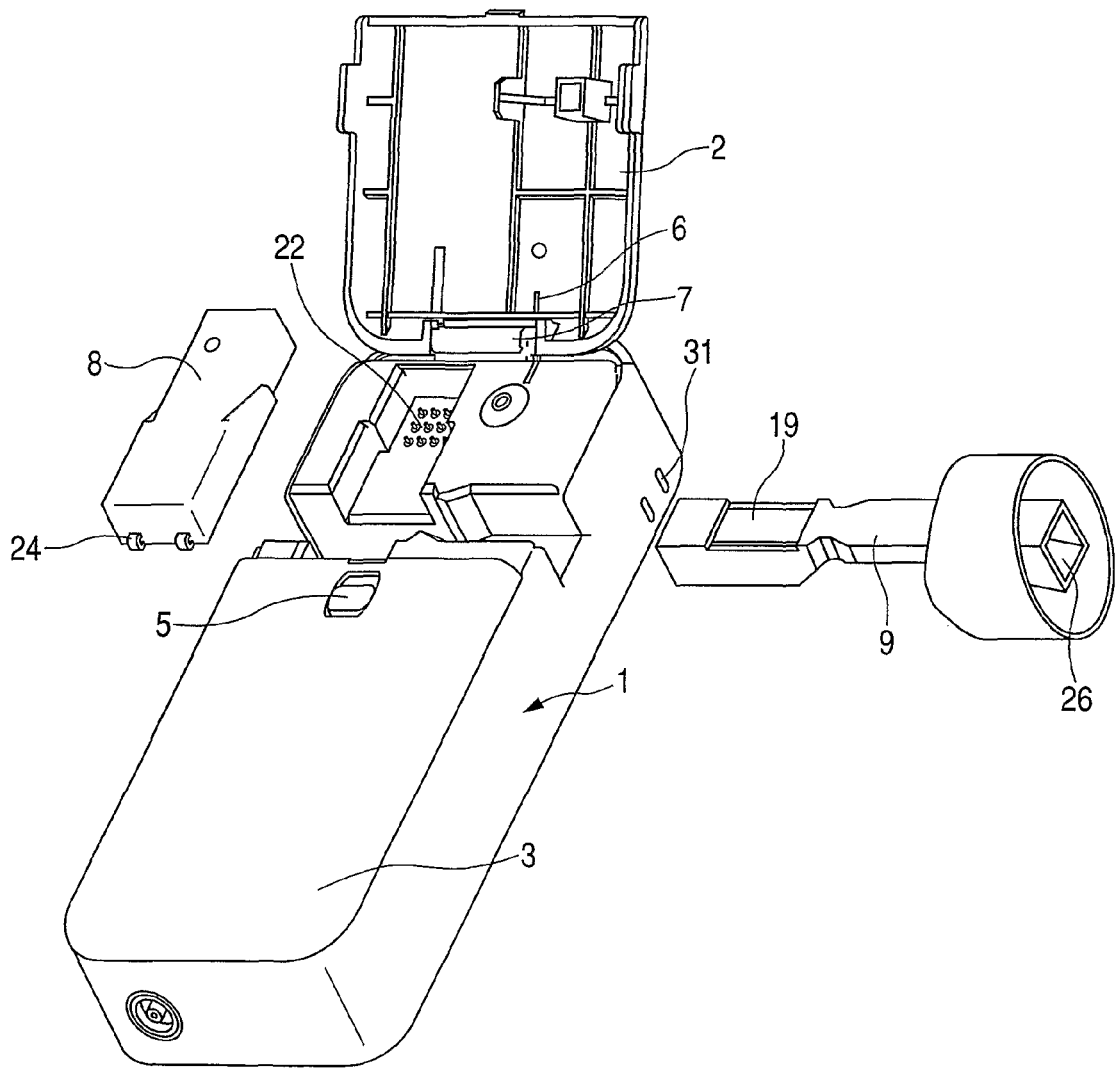
FIG. 2 is a perspective view for illustrating a state in which an access cover is open in the example shown in FIG. 1.

FIG. 2 shows a state in which the access cover 2 is open. In a state in which the access cover 2 is open, it is possible to access the inside of the ejection device, thereby making it possible to attach a drug ejection unit 8 including a tank containing the drug and a mouthpiece 9 used in inhalation by a user to the ejection device main body 1. The mouthpiece 9 is attached below the ejection unit 8, and they are attached so as to cross each other. In use, after the drug ejection unit 8 and the mouthpiece 9 are attached as described above, the access cover 2 is closed and the user uses the ejection device.

From the viewpoint of hygiene, it is desirable that the drug ejection unit 8 and the mouthpiece 9 are disposable or regularly replaced, so that they may be configured to be integrated into a single member.

Figure 3:
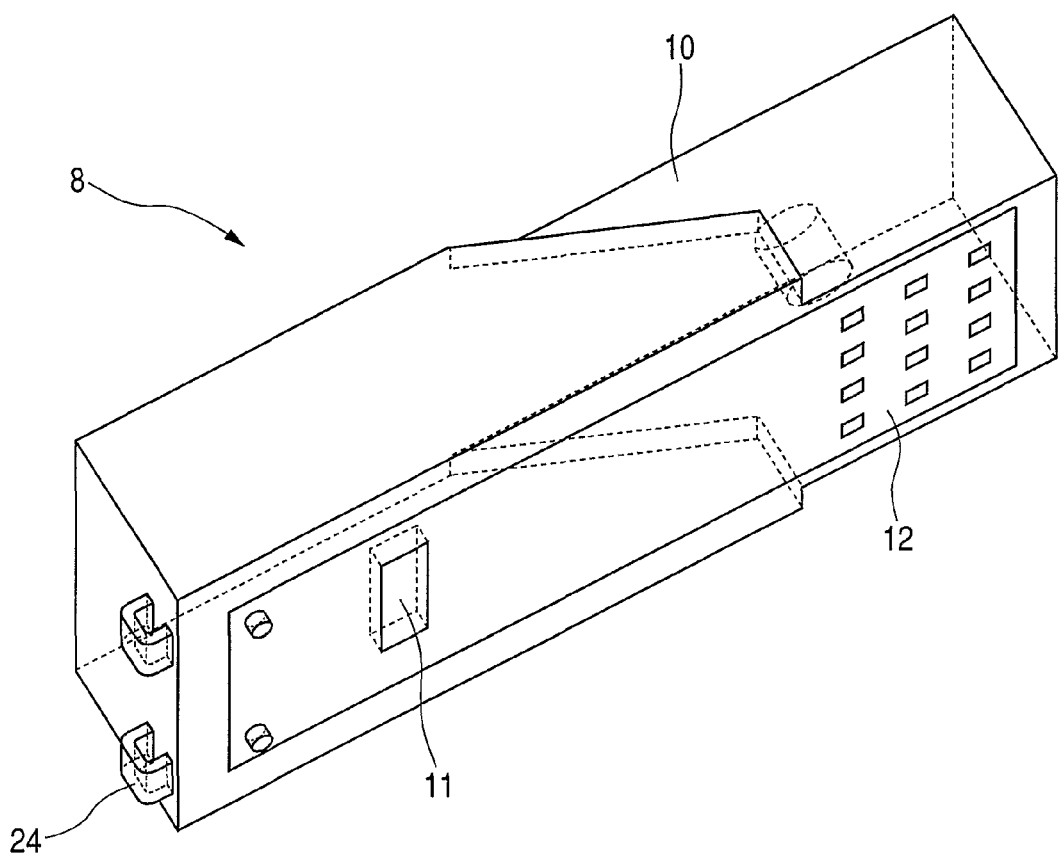
FIG. 3 is a perspective view for illustrating an ejection unit used in the example shown in FIG. 1.

The ejection unit 8 as a whole is shown in FIG. 3. The ejection unit 8 includes a tank 10 for containing the drug, a head portion (ejection portion) 11 for ejecting the drug, an electric connection surface 12 for supplying to a heater provided in the head portion 11 an electric power for imparting thermal energy for producing bubbles from a battery (not shown), and the like. Incidentally, the configuration of the head portion 11 is not limited to this, and a configuration may be adopted in which a piezoelectric element is provided in place of the heater.

When the ejection unit 8 is attached to the device main body 1, terminals of the electric connection surface 12 of the ejection unit 8 are electrically connected to corresponding terminals of an electric connection surface 22 (see FIG. 2) of the device main body 1. The battery is rechargeable, for example, as a secondary battery retaining the electric power for imparting energy to the heater or the like in the ejection device. A front surface portion of the ejection unit 8 can rotate about a hinge portion 24 to be opened, thereby making it possible to access the tank 10. Further, the head portion 11 of the ejection unit 8 is, when attached, exposed through an opening portion 19 (see FIG. 2) of the mouthpiece 9 to the inside of an inhalation flow path 20 (see FIG. 4) formed in the mouthpiece 9. Accordingly, liquid droplets ejected from the head portion 11 can enter the inhalation flow path 20 of the mouthpiece 9.

Figure 4:
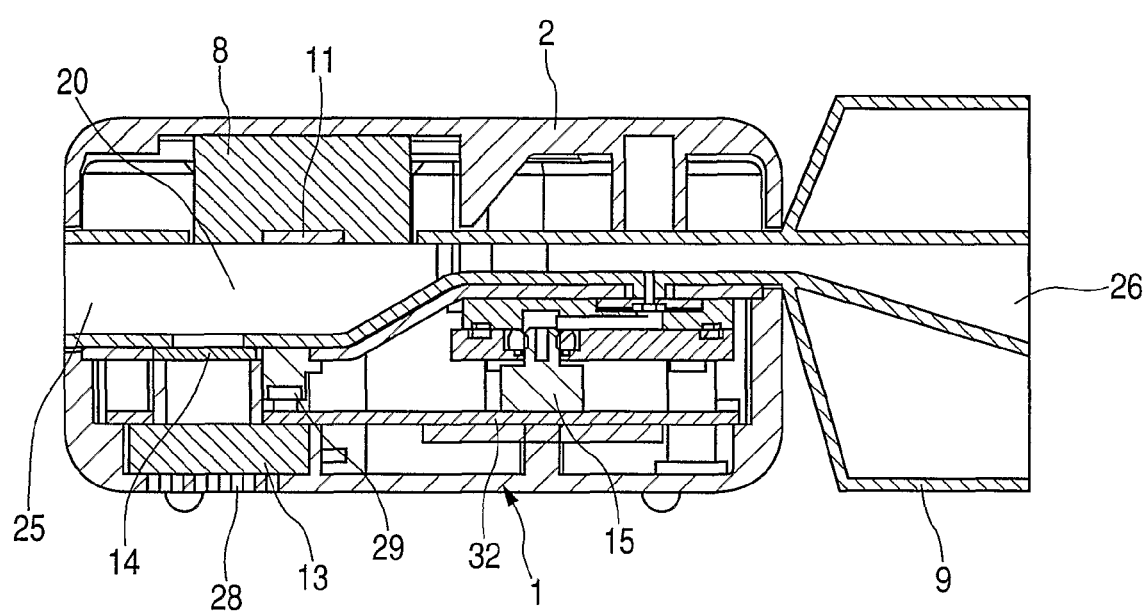
FIG. 4 is a cross-sectional view of the ejection device of the example of FIG. 1 for illustrating a discharger.
Figure 5:
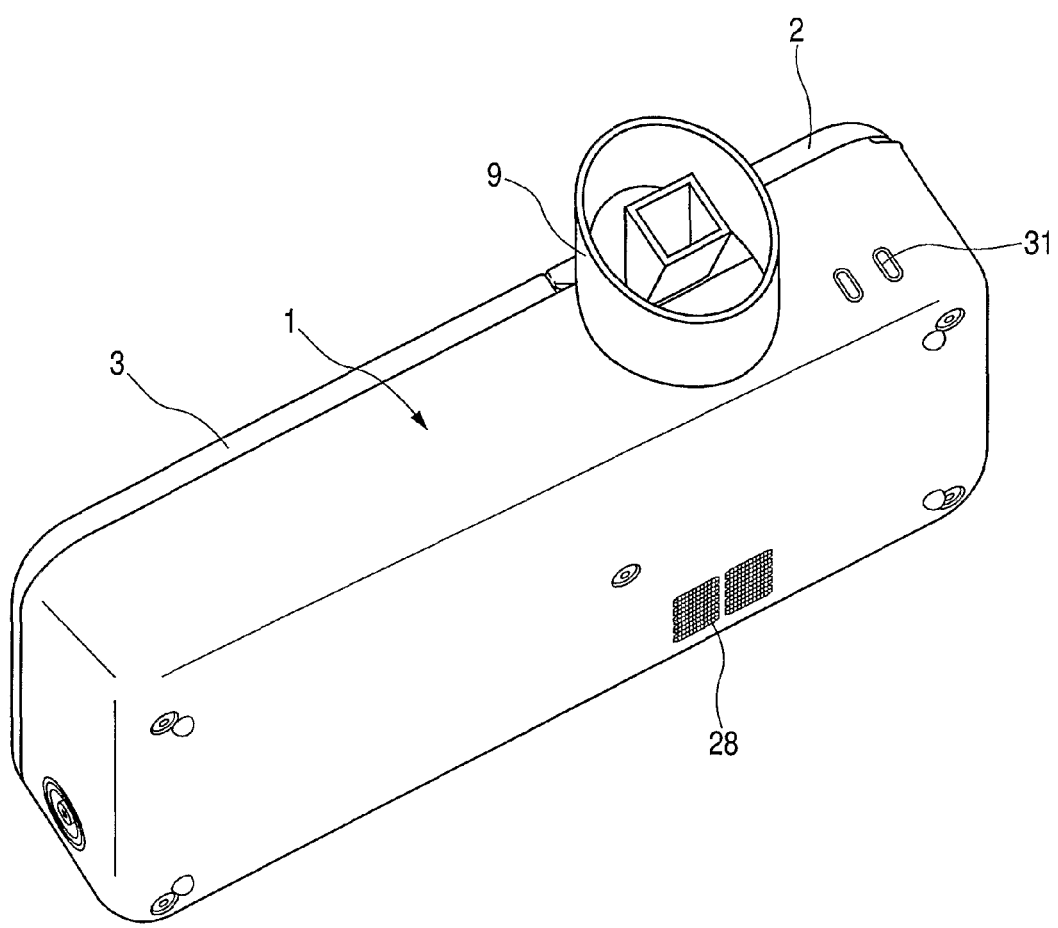
FIG. 5 is a perspective view of the ejection device of the example of FIG. 1 as seen from the rear surface side thereof.
Figure 6:
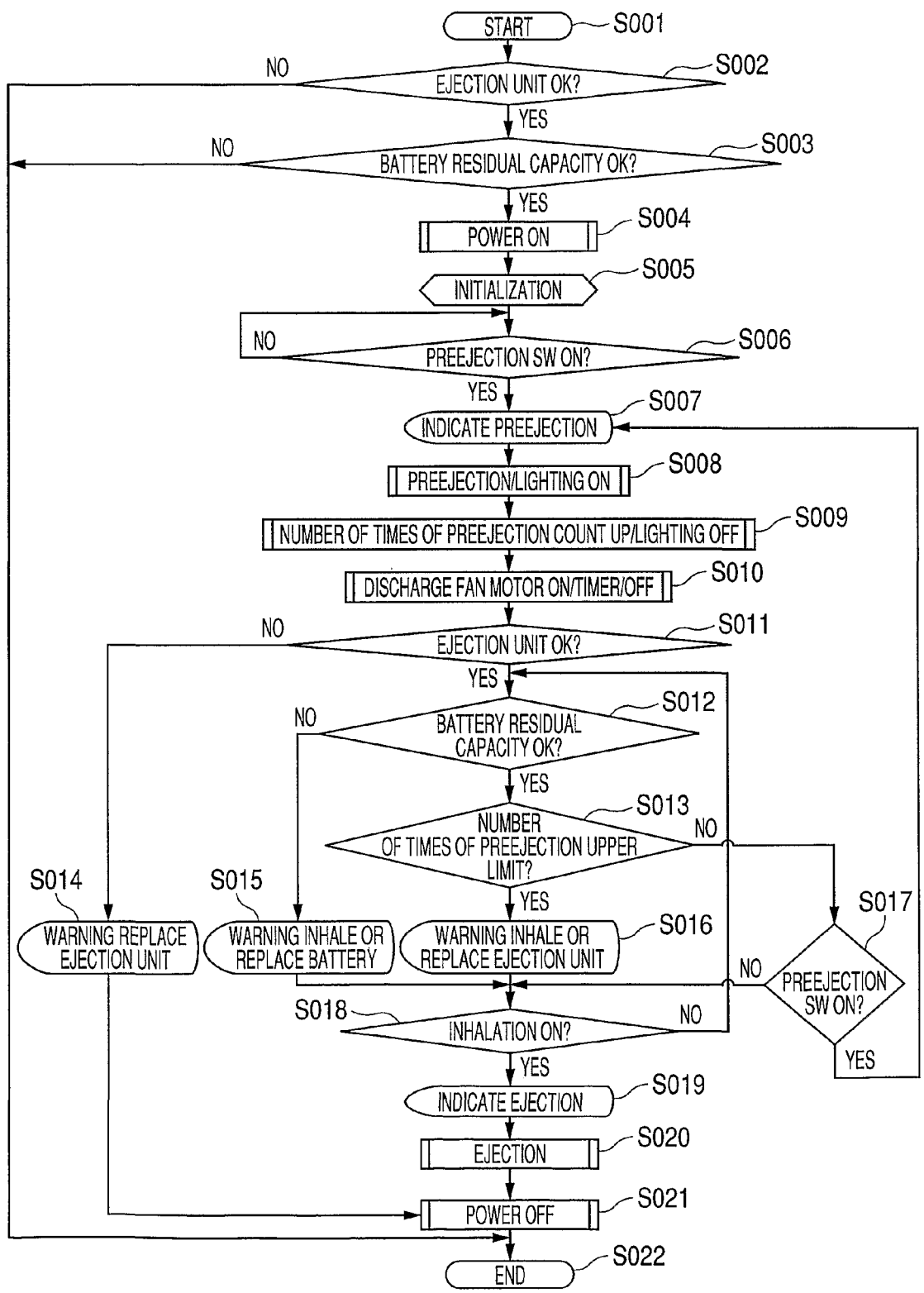
FIG. 6 is a flow chart showing an operation procedure in the example shown in FIG. 1.

FIG. 4 is a cross-sectional view of the device cut along the inhalation flow path 20. The inhalation flow path 20 is formed of an inner wall of the mouthpiece 9 for preventing the inside of the main body from being soiled. In the figure, reference numeral 25 denotes an air intake port of the inhalation flow path 20 and reference numeral 26 denotes an inhalation port. When an inhalation operation is performed, the drug ejected from the drug ejection unit 8 and formed into liquid droplets is carried by means of an air flow generated by the inhalation operation from the air intake port 25 to the inhalation port 26 to thereby be taken in a human body through the inhalation flow path 20 of the mouthpiece 9.

The air intake port 25 is formed such that an ejection-orifice-provided surface of the head portion 11 of the drug ejection unit 8 is positioned perpendicularly to the air intake port 25. Accordingly, the liquid droplets ejected into the inhalation flow path 20 from the ejection orifice can be observed from the outside.

Liquid droplet ejection at a time of normal drug inhalation is started when detection means such as a negative pressure sensor 15 detects an inhalation operation of the user, in conjunction with the inhalation operation. On the other hand, the preejection of liquid droplets is started by a switch operation or the like, by which a user can arbitrarily instruct the starting. Alternatively, setting may be made such that after the device main body is energized, a preejection is automatically started. In these cases, the air flow as described above does not occur in the inhalation flow path 20 of the mouthpiece 9, so the ejected drug drifts in a form of mist. The drug liquid droplets ejected in the preejection and drifting in the form of mist in this way are illuminated by a light source 29, and can be observed from the outside of the ejection device through the air intake port 25. Thereby, the user can visually confirm whether or not the preejection is being performed.

Liquid droplets ejected by the preejection and drifting in the form of mist are immediately evacuated from the inhalation flow path 20 by means of a discharge (exhaust) air flow generated by driving a fan motor 13 provided just under the ejection orifice of the head portion 11 of the drug ejection unit 8. The liquid droplets are collected by a filter 14 disposed on a front surface of the fan motor 13. Only air which does not contain the liquid droplets passes through a discharge port 28 (see FIGS. 4 and 5) provided in a rear surface of the ejection device main body 1 to be discharged to the outside. Here, it is preferable that the discharger is disposed so as to face the ejection head. With such disposition, the liquid droplets ejected by the preejection can be guided to the discharger more easily, thereby making it possible to reduce adhesion of the liquid droplets to the inside of the flow path.

Further, it is preferable to set the fan motor 13 to be automatically driven in conjunction with the preejection. This enables to effectively discharge the liquid droplets.

It is desirable that the filter 14 can be easily replaced. Further, in a case where the mouthpiece 9 is designed to be disposable, the filter 14 may be integrated with the mouthpiece 9 into a single body. Incidentally, reference numeral 32 denotes a control board for controlling various operations of the ejection device.

For discharging liquid droplets ejected by a preejection, the following methods are available. Liquid droplets are usually charged positively, so that it is possible to intake the liquid droplets using an absorbing member which is negatively charged. Here, it is difficult to intake the liquid droplets only with an electrostatic attraction force. Therefore, it is preferable that a button exposed to the outside or the like is pressed to physically deform a certain portion so that an air flow from the inside of the inhalation flow path 20 toward the absorbing member is generated, thereby allowing the liquid droplets to be drawn into the absorbing member.

According to the configuration of the present example, in a case where preejection is performed before inhalation, liquid droplets ejected by the preejection are not released to the outside of the device, and no liquid droplet remains to drift therein. As a result, it is possible not only to stabilize the amount of inhalation to improve the reliability of the inhalation but also to eliminate the possibility that another person requiring no drug administration may accidentally inhale liquid droplets of a drug. Thus, the ejection device does not affect the surroundings, so that it is possible for a user to hygienically perform inhalation anywhere at ease.

The ejector according to the present invention includes, but not limited to, a metered dose inhaler (MDI) system, a nebulizer system, and an ink jet system. Of them, the preferred are those having an ejection head which utilizes a thermal energy or piezoelectric energy to eject a drug. An example thereof is the ink jet system which is capable of digitally controlling ejection conditions of the fine liquid droplets. More preferable example thereof is a thermal ink jet system which allows the number of ejection orifices provided per unit area to be increased and significantly reduces the production cost.

According to the above-mentioned inhalation device, a user can always inhale a drug with a constant particle diameter. Accordingly, without a reduction in the amount of the drug inhaled and a fear of contamination due to adhesion of the drug, it is possible to obtain reproducibility of the effect of the drug independently of how the user inhales the drug.

FIG. 6 is a flow chart showing an example of usage of the ejection device 1.

First, owing to an operation such as pressing of a power switch by a user, the ejection device is started to use (S001). After the ejection device is started to use, the presence/absence of the drug ejection unit 8 is checked (S002), and if it is absent, the operation ends without any progress (S022).

The detection means for the drug ejection unit 8 can be realized by, for example, when the drug ejection unit 8 performs ejection by the thermal ink jet system, measuring the resistance value of a heater serving as an ejection energy generating means.

When the drug ejection unit 8 is present, the residual capacity of a battery is checked (S003), and if it is insufficient, the operation ends (S022). In this case, indication of promoting replacement or recharging of the battery may be made using the indication LED 31 or the like. If it is determined that the battery residual capacity is available to perform at least one preejection and at least one inhalation operation, the power is turned on (S004) and initialization is performed (S005). In a case where the drug ejection unit 8 is of a disposable type, at the stage of the initialization (S005), the number of times of the preejection operations is reset.

After completion of the initialization (S005), in order to improve the ejection reliability, it is necessary to perform preejection at least once. Accordingly, judgment on whether or not a preejection switch is on (S006) may be automated.

In this way, when starting of the preejection is directed automatically or manually, an indication of notifying the user that the preejection is being performed (S007) is made and the preejection and lighting of the light source 29 is conducted (S008).

Although there are many cases where it is sufficient that the preejection is performed at least once, the ejection device of the present example has a configuration such that the preejection can be performed a plurality of times in accordance with the need of the user. However, also in this case, the following considerations are required. In the preejection, it is assumed that according to the type, prescription, additive or the like of a drug, ejection conditions suitable for visual observation such as driving frequency and driving time are different from those of normal ejection. When the ejection conditions are different, the amount of the drug and the electric power consumed in the preejection will vary. Accordingly, in order to ensure the amount of the drug required for at least one inhalation, a control function of limiting the number of preejections by the user's operation is required. With regard to the amount of the drug, it is desirable that the amount of the drug consumed in the preejection is less than the amount of the drug required for the inhalation. Here, when it is assumed that A represents an amount necessary for inhalation, B represents an amount consumed in a single preejection, and C represents a total amount stored in the drug ejection unit 8 or a maximum amount used in a single operation, the preejection is allowed to be performed up to $(C-A)/B$ ($>1$) times. After completion of the preejection, the number of times of the preejection operation derived above is counted up (S009). After the completion of the preejection, the light source 29 is turned off.

Further, after the completion of the preejection, in order to collect liquid droplets ejected by the preejection, the fan motor 13 is driven for a period of time suitable for collecting the liquid droplets. The driving time period of the fan motor may be made variable according to the type of the ejected drug and the preejection amount. Further, concurrently with or immediately after the start of the preejection, the driving of the fan motor 13 may be started.

Because there is a possibility that some abnormality may be caused in the drug ejection unit 8 due to the preejection to thereby interfere with the inhalation, the ejection device main body 1 is provided with an inspection means for the drug ejection unit 8, and after the completion of the preejection, the drug ejection unit 8 is inspected (S011). The inspection means itself may be the same as the means for checking the presence/absence of the drug ejection unit 8 in the drug ejection unit check (S002). When it is determined that an abnormality is present in the drug ejection unit 8, the user is notified of the abnormality, and the replacement of the unit is promoted (S014).

Next, as with the residual amount of the drug, in order to ensure an electric power required for at least one inhalation, similarly as the step (S003), the battery residual capacity is checked (S012). When a determination is made that the battery residual capacity cannot afford to perform preejection any more, an indication of advising immediate inhalation operation or promoting the replacement of the battery is made (S015).

When the battery residual capacity is sufficient, a judgment on whether or not the number of times of the preejection has reached the upper limit of (C−A)/B times is performed (S013). When the number of times of the preejection does not reach the upper limit, processes from monitoring of the preejection switch (S017) to monitoring of the inhalation (S018) are repeated. When the preejection switch is turned on (this normally depends on the operation of the user), the indication that the preejection is being performed (S007) and the subsequent process (steps) are repeated.

By repeating the preejection operation, the number of times of the preejection eventually reaches the upper limit. In this case, an indication of advising immediate inhalation operation or promoting the replacement of the drug ejection unit 8 is made (S016) to wait for the start of the inhalation.

When the detection means such as the negative pressure sensor 15 detects the inhalation, an indication of notifying the user that the ejection is performed is made (S019), the ejection is performed (S020), and then the power is turned off (S021), thereby reaching the end (S022).

In a case where the drug ejection unit 8 is not of a disposable type, at the stage of power off (S021) or end (S022), histories of the number of times of preejection operations and the number of times of inhalation are stored.

Further, after the completion of the ejection (S020), checking for the drug ejection unit 8, which is the same as that in the steps (S002/S001), or checking for the battery residual capacity, which is the same as that in the steps (S003/S012), may be performed.

The present invention is not limited to the above embodiments and various changes and modifications can be made within the spirit and scope of the present invention. Therefore to apprise the public of the scope of the present invention, the following claims are made.

This application claims priority from Japanese Patent Application No. 2005-264535 filed Sep. 13, 2005, which is hereby incorporated by reference herein.

The invention claimed is:

1. A drug ejection device for ejecting a drug in a form of liquid droplets into an inhalation flow path and allowing a user to inhale the drug, comprising:
   a main body;
   a mouthpiece attachable to the main body and forming the inhalation flow path in cooperation with the main body;
   an ejector for performing normal drug ejection for inhalation and drug pre-ejection not for inhalation; and
   a discharger for removing drug liquid droplets ejected by the drug pre-ejection and drug liquid droplets drifting in the inhalation flow path from inside the inhalation flow path,
   wherein the discharger has an exhaust fan and a drug liquid droplet collecting filter constituted integrally with the mouthpiece and is disposed facing the ejector with the inhalation flow path therebetween, and
   wherein a driving time period of the exhaust fan is variable according to a type of the ejected drug.

2. The drug ejection device according to claim 1, wherein the discharger is automatically driven in conjunction with the liquid droplet pre-ejection.

3. The drug ejection device according to claim 1, wherein the discharger comprises an exhaust fan.

4. The drug ejection device according to claim 1, wherein the ejector comprises an ejection head for ejecting the drug by utilizing thermal energy or piezoelectric energy.

* * * * *